United States Patent
Wohlschlager et al.

(10) Patent No.: US 11,304,643 B2
(45) Date of Patent: Apr. 19, 2022

(54) MATERNAL MONITORING TRANSDUCER AND OPERATING METHOD

(71) Applicant: KONINKLIJKE PHILIPS N.V., Eindhoven (NL)

(72) Inventors: Markus Wohlschlager, Sindelfingen (DE); Manuel Stephan, Kusterdingen (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 77 days.

(21) Appl. No.: 16/323,548

(22) PCT Filed: Aug. 7, 2017

(86) PCT No.: PCT/EP2017/069878
§ 371 (c)(1),
(2) Date: Feb. 6, 2019

(87) PCT Pub. No.: WO2018/029120
PCT Pub. Date: Feb. 15, 2018

(65) Prior Publication Data
US 2019/0192027 A1 Jun. 27, 2019

(30) Foreign Application Priority Data
Aug. 9, 2016 (EP) .................................... 16183441

(51) Int. Cl.
*A61B 5/288* (2021.01)
*A61B 5/024* (2006.01)
(Continued)

(52) U.S. Cl.
CPC ............ *A61B 5/288* (2021.01); *A61B 5/0011* (2013.01); *A61B 5/02411* (2013.01);
(Continued)

(58) Field of Classification Search
CPC . A61B 5/0448; A61B 5/0011; A61B 5/02411; A61B 5/02438; A61B 5/11;
(Continued)

(56) References Cited

U.S. PATENT DOCUMENTS 3,945,373 A    3/1976   Tweed
5,115,292 A * 5/1992   Takebe ................ G01P 15/0802
                                                     257/254
(Continued)

FOREIGN PATENT DOCUMENTS

EP    1931184    6/2008
EP    3017762    5/2016
(Continued)

*Primary Examiner* — Christopher A Flory (57) ABSTRACT

The present disclosure relates to a maternal monitoring transducer (20), comprising a housing (60), a substrate board (72), particularly a PCB (70), disposed in the housing (60) and comprising control components (74), and a displacement measurement arrangement (76) comprising a displacement-sensitive structure (78) that is arranged to detect deformations of a deflectable measurement section (80) of the substrate board (72), wherein the maternal monitoring transducer (20) supplies a signal that is representative of maternal motion. The disclosure further relates to a method of operating a maternal monitoring transducer (20).

20 Claims, 6 Drawing Sheets

(51) Int. Cl.
*A61B 5/11* (2006.01)
*A61B 5/00* (2006.01)

(52) U.S. Cl.
CPC ............ *A61B 5/02438* (2013.01); *A61B 5/11* (2013.01); *A61B 5/4356* (2013.01); *A61B 5/4362* (2013.01); *A61B 5/6823* (2013.01); *A61B 5/6833* (2013.01); *A61B 5/7203* (2013.01); *A61B 2560/0247* (2013.01); *A61B 2562/0219* (2013.01); *A61B 2562/0261* (2013.01)

(58) Field of Classification Search
CPC ... A61B 5/4356; A61B 5/4362; A61B 5/6823; A61B 5/6833; A61B 5/7203; A61B 2560/0247; A61B 2560/0219; A61B 2560/0261

See application file for complete search history.

(56) References Cited

U.S. PATENT DOCUMENTS

| | | |
|---|---|---|
| 5,865,733 A | 2/1999 | Malinouskas |
| 5,913,826 A * | 6/1999 | Blank ................ A61B 5/02007 600/500 |
| 6,341,532 B1 * | 1/2002 | Xu .......................... G01L 1/148 73/147 |
| 2009/0054793 A1 * | 2/2009 | Nunez .................... A61N 1/057 600/485 |
| 2009/0149038 A1 * | 6/2009 | Gabara .................... H01L 24/95 439/55 |
| 2010/0043546 A1 * | 2/2010 | Kandori ............. G01P 15/0802 73/504.12 |
| 2010/0097776 A1 * | 4/2010 | Gabara ............. B01L 3/502715 361/792 |
| 2010/0191154 A1 * | 7/2010 | Berger .................... A61B 5/742 600/595 |
| 2011/0295102 A1 | 12/2011 | Lakkis |
| 2013/0310710 A1 * | 11/2013 | Eswaran .............. A61B 5/4362 600/591 |
| 2014/0296749 A1 | 10/2014 | Reid |
| 2015/0339001 A1 | 11/2015 | Zirkl |

FOREIGN PATENT DOCUMENTS

| | | |
|---|---|---|
| WO | 2006006107 | 1/2006 |
| WO | 2008/010216 | 1/2008 |
| WO | 2013071095 | 5/2013 |
| WO | 2014045221 | 3/2014 |

* cited by examiner

MATERNAL MONITORING TRANSDUCER AND OPERATING METHOD

CROSS REFERENCE TO RELATED APPLICATIONS

This application is the U.S. National Phase application under 35 U.S.C. § 371 of International Application No. PCT/EP2017/069878 filed Aug. 7, 2017, published as WO 2018/029120 on Feb. 15, 2018, which claims the benefit of European Patent Application Number 16183441.1 filed Aug. 9, 2016. These applications are hereby incorporated by reference herein.

FIELD OF THE INVENTION

The present invention relates to a maternal monitoring transducer and to a method of operating a maternal monitoring transducer. More particularly, but not intended to limit the scope of the invention, the present disclosure relates to improvements in cardiotocography devices and methods, particularly so-called tocodynamometers.

BACKGROUND OF THE INVENTION

Pregnancy monitoring which may be also referred to as fetal monitoring and/or labor monitoring is commonly used in late stages of pregnancy. By way of example, during labor, physiological parameters such as fetal heart rate may be monitored so as to identify signs of fetal distress and/or fetal well-being. Prior to labor, the mother-to-be may undergo one or more medical ultrasound examinations, thereby providing fetal heart rate information, fetal movement information, fetal size information and similar information that is used to identify markers of fetal growth during pregnancy. During labor and birth, also uterine activity, particularly uterine contractions, are frequently monitored.

In gynecology and obstetrics, generally two medical parameters are important to assess the condition of the fetus and the state of delivery. These two parameters are the fetal beat-to-beat heart rate, e.g. measured via an ultrasound Doppler signal, and uterus (or labor) activity. Simultaneous assessment and correlation of the fetal heart rate (FHR) and uterine activity allows an exact determination of the fetal condition. Monitoring systems that are capable of detecting both parameters are frequently referred to as cardiotocographs (CTG monitors). Further, also fetal movement is considered as an indicative parameter for assessing the condition of the fetus.

By way of example, a conventional CTG device (cardiotocography device) may contain an ultrasound Doppler transducer (US transducer) for measuring fetal heart rate (FHR) and detecting fetal movements, as well as a pressure transducer (also called toco transducer, or tocodynamometer) for measuring uterine activity.

Each of the transducers may be placed at the abdomen of the mother, e.g. by an elastic belt fitted around the waist or by an adhesive tape or patch. Each of the transducers may be arranged inside a respective probe. Particularly the ultrasound transducer may be manually placed and positioned so as to seek for a considerably strong signal, e.g. a considerably strong heart beat or heart rate signal. An ideal position of the ultrasound transducer at the expectant mother's abdomen may depend on an actual orientation of the fetus and an actual posture of the mother.

Monitoring the uterine activity is of importance during labor and fetal expulsion. Depending on the intervals of occurrence, intensity, timing patterns and waveform shapes of uterine contractions in connection with the also recorded fetal heart rate, obstetricians can make decisions, for example about possible administration of medication. As indicated above, a common method for noninvasively deriving this information is the use of a so-called tocodynamometer. The tocodynamometer is placed on the abdominal wall and, for instance, held in position with an elastic belt. Tension changes of the uterine muscle during a contraction are registered by a sensitive area arranged in the middle of the sensor housing. The sensitive area is surrounded by a stiff guard ring in order to reduce the influence of overall movement and breathing artifacts.

Several approaches to tocodynamometer design have been proposed, including electromechanical sensor arrangements, pneumatic sensor arrangements, and strain gauge sensor arrangements. By way of example, U.S. Pat. No. 3,945,373 A discloses a tocodynamometer comprising an electro-optical transducer, and EP 3 017 762 A1 discloses a pneumatic tocodynamometer.

In some tocodynamometers, due to their sensitivity and stability, the conversion of the pressure force to an electrical signal is done by metal strain gauge elements. An important component of this design is the strain gauge element. However, numerous elaborate manufacturing steps for this device like cutting, sputtering, etching, coating and final trimming are required which render the strain gauge element expensive. Further, due to the complex design, the design approach based on metal strain gauge elements is prone to quality variations.

Measuring uterine activity with external sensors that are placed on the abdomen is generally susceptible to sudden and unexpected offset and sensitivity changes. This may involve a temperate drift of the strain gauge element, for instance. Typically, offset and sensitivity of the strain gauge element has to be controlled and adjusted by manual user interaction. To this end, separate operation steps and control elements are required, e.g. control buttons at the transducer's housing.

If the adjustment remains undone, consequences may involve clipped or flat contraction traces on the resulting measurement plot. The permanent re-adjustment and offset control causes additional workload and unnecessary stress for a user, particularly the caregiver.

Hence, there is thus still room for improvement in maternal monitoring transducers, particularly uterine activity transducers.

SUMMARY OF THE INVENTION

In view of the afore-going, it is an object of the present disclosure to provide an improved maternal monitoring transducer, particularly a tocodynamometer transducer for measuring uterine activity, that enables a precise detection of maternal motion, involving a considerable degree of accuracy and sensitivity. Further, it would be advantageous to provide a maternal monitoring transducer that is easy to operate. Preferably, manual adjustment and setting operations can be widely dispensed with. Further, it would be beneficial to provide a maternal monitoring transducer that is easy to assemble and easy to manufacture. Preferably, the maternal monitoring transducer is configured in a cost-saving but still reliable and sensitive fashion.

It is a further object of the present disclosure to provide for a maternal and fetal monitoring system that incorporates a respective maternal monitoring transducer. Further, it is an object of the present disclosure to present a method of operating a maternal monitoring transducer.

In a first aspect of the present disclosure, a maternal monitoring transducer is presented, the transducer comprising:
- a housing,
- a substrate board, particularly a PCB, disposed in the housing and comprising a deflectable measurement section, which is integrally formed in the substrate board, and circuitry components, and
- a displacement measurement arrangement arranged at the substrate board and comprising a displacement-sensitive structure that is arranged to detect deformations of the deflectable measurement section of the substrate board, wherein the maternal monitoring transducer is arranged to supply a maternal uterine-activity indicative signal that is representative of maternal motion and is based on the detected deformations.

This aspect is based on the insight that the substrate board, particularly the printed circuit board (PCB), that is anyway provided in the transducer may be used to incorporate the measurement arrangement therein, at least in part. Such a substrate board comprises circuitry components, which at least in part enable the sensing functionality of the transducer. In other words, the substrate board itself is used to (mechanically) sense the maternal motion. At the substrate board, at least one displacement-sensitive structure is provided as an integrally part of said substrate which is arranged to be deflected or deformed in response to external motion events, for instance induced by muscular uterine activity. The displacement-sensitive structure is exposed to the maternal motion events.

As a consequence, no separate, distinct displacement-measurement sensor is provided that is an additional attachment component. Rather, at least a part of the displacement measurement arrangement is integrally formed with the substrate board. By way of example, a deformable lug or tab may be defined at the substrate board. The deformable lug may be coupled with a sensing section of the transducer that contacts an abdominal portion of the (female) patient. Hence, the displacement-sensitive structure may be deformed or deflected, wherein a deformation degree may be sensed by appropriate components. The advantage of such a displacement measurement arrangement is a reduction in the transducer component's as well as its cost.

The substrate board may be arranged as a fiber reinforced epoxy board. An example for an appropriate material is FR4 based on which printed circuit boards may be formed. The material from which the substrate board is typically formed is at least partially deflectable in a considerably resilient and elastic fashion. Hence, the material for the substrate board is well suited for deflection/deformation measurement. As the deflectable measurement section of the substrate board is an integrally formed part of the substrate board, the displacement measurement arrangement is arranged as an integrated component and not as a separate component that is merely attached to or connected with the substrate board.

The maternal monitoring transducer may be also referred to as tocodynamometer. The maternal monitoring transducer may form a part of a CTG monitoring system. Typically, maternal motion involves muscular uterine activity or uterine contractions.

The displacement-sensitive structure may be arranged as strain-sensitive structure, deflection-sensitive structure and/or motion-sensitive structure.

In accordance with the above-presented aspect, an integrated displacement measurement may be provided which does not require additional, separate displacement sensors that do not use the deformability and/or flexibility of the substrate board material.

The above-presented aspect has the further advantage that standard PCB processes may be used to configure and manufacture the displacement sensing element. Further, a direct integration of the displacement-sensitive structure is achieved which is cost saving and installation space saving. A further benefit is that the number of separate assembly components may be reduced. Further, an increased freedom of design is provided as design restrictions that are inherent to conventional transducers may be overcome. Particularly the housing of the maternal monitoring transducer may be arranged in a more compact fashion.

A further benefit is that more than only one displacement-sensitive structure and, accordingly, displacement measurement arrangement may be provided at the substrate board. Hence, maternal motion monitoring may be even more sensitive, for instance involving multiaxial measurements.

A further advantage of the presented approach is that the circuitry components may include at least one signal processing controller enabling software-based automatic signal compensation or correction measures, involving gain adjustment and offset adjustment. This may have the advantage that manual adjustment and working steps, particularly for baseline correction, may be reduced or even avoided.

As a result, the signal provided by the maternal monitoring transducer may be already automatically processed and fitted without manual intervention.

In one exemplary embodiment, the transducer is arranged as a pressure-sensitive maternal monitoring transducer that detects maternal uterine activity indicative information. In other words, the transducer may be arranged as a tocodynamometer transducer. The displacement measurement arrangement may be configured for sensing and monitoring uterine contractions which are indicative of labor.

By way of example, the displacement measurement arrangement may involve a magnetic/inductive displacement sensor. Further, in another exemplary embodiment, the displacement measurement arrangement may involve a capacitive displacement sensor. In yet another exemplary embodiment, the displacement measurement arrangement may involve a conductive deformation sensor. For instance, the conductive deformation sensor may use conductive tracks or traces, wherein the conductivity thereof is dependent on a degree of deformation/deflection of the measurement section of the substrate board.

In yet another exemplary embodiment of the transducer, the displacement measurement arrangement is arranged at the substrate board, wherein the deflectable measurement section is integrally formed in the substrate board. Therefore, the substrate board, particularly the PCB, itself may be deformed so as to detect the maternal motion. The support board forms an integral part of the displacement measurement arrangement.

In yet another exemplary embodiment of the transducer, the displacement-sensitive structure of the displacement measurement arrangement is directly attached to the substrate board. This may involve, for instance, that a coil or an electrode is attached to the surface of the substrate board. Needless to say, the displacement-sensitive structure may be also integrally formed with the substrate board.

In yet another exemplary arrangement, the displacement-sensitive structure of the displacement measurement arrangement is embedded in the substrate board. For instance, integral conductive layers may be provided at the substrate board that define an electrode, a coil and/or a conductive track.

In another exemplary embodiment of the transducer, the deflectable measurement section is defined by a circumscribing recess that increases the deformability of a residual transitional portion of the substrate board. In other words, the measurement section may be arranged as a lug that forms a deflectable or deformable arm. The recess forms a gap that separates the measurement section from surrounding portions of the substrate board. Consequently, the overall stability and strength of the substrate board is maintained, while the deformability of the transitional portion is deliberately increased. As a consequence, the measurement sensitivity is even further improved. In a further exemplary embodiment, the deflectable measurement section is arranged in a central portion of the substrate structure.

In yet another embodiment of the transducer, the deflectable measurement section is operatively coupled with a contact section that contacts an abdominal portion when the transducer is applied to a maternal patient. For instance, the transducer may be attached to the abdominal portion and secured by a tape, patch, strap or belt. In this way, the contact section is exposed to and may sense, at the abdomen, contractions that are caused by uterine activity (labor contractions). The deflectable measurement section may be mechanically linked with the contact section. Hence, external movements may be transferred to the measurement section. The contact section may be arranged at or form part of the housing.

Preferably, the transducer is a movable compact design transducer that may be basically freely positioned at the abdominal portion of the maternal patient. Hence, depending on the actual posture of the patient, the transducer may be attached at an appropriate position that is suitable for measuring uterine contractions.

In yet another exemplary embodiment of the transducer, the displacement-sensitive structure comprises an inductive coil and a reference element, wherein an actuation of the deflectable measurement section involves relative motion between the inductive coil and the reference element. In this way, an inductive displacement sensor may be provided. Preferably, the conductive coil is embedded in or directly formed at the substrate board. Hence, a deflection of the deflectable measurement section involves a movement of the inductive coil with respect to the reference element.

The inductive sensor may be arranged as a non-contact proximity sensor. The reference element may be arranged as a conductive reference element which may be made from ferrous metal and from non-ferrous metal. For instance, the reference element may be made from aluminum or an aluminum alloy. Electric current in the coil generates a magnetic field, wherein a relative movement between the inductive coil and the reference element influences the magnetic field and the inductance of the coil. This change can be detected by appropriate sensing circuitry which may be as well provided at the substrate board.

In yet another exemplary embodiment of the transducer, the displacement-sensitive structure comprises a trace or coil to which constant current is applied in order to generate a magnetic field. For instance, the coil/trace may be arranged at the deflectable measurement section of the substrate board and a Hall-Effect sensor or a similar sensor may be used that is placed at a defined distance for measuring changes of the magnetic field which are attributable to a deflection of the deflectable measurement section. For instance, the sensor may be placed at or connected with the substrate board as well, preferably at a relatively fixedly attached (i.e. non-deflectable) portion thereof that is spaced away from the deflectable measurement section. In a further exemplary embodiment, a permanent magnet is used that is similarly arranged at the deflectable measurement section.

In yet another exemplary embodiment of the transducer, the displacement-sensitive structure comprises a movable electrode and a reference electrode, wherein an actuation of the deflectable measurement section involves relative motion between the movable electrode and the reference electrode. Hence, the movable electrode and the reference electrode may form a capacitive displacement/proximity sensor. Preferably, the movable electrode is provided at and/or attached to the deflectable measurement section in an integrally formed fashion.

The two electrodes are spaced from one another and define a capacitor the capacitance thereof is dependent on the actual distance between the two electrodes. A capacitance-based sensor is accurate and capable of high-resolution sensing.

In yet another exemplary embodiment of the transducer, the displacement-sensitive structure comprises at least one conductive track that is associated with the deflectable measurement section. By way of example, the conductive track may be arranged as a conductive polymer track. The track may involve a pattern that ensures a certain effective length of the track. Preferably, the at least one conductive track is arranged at the deformable transitional portion. The conductive track does not necessarily cooperate with a reference element. Rather, the deflection and/or deformation of the deformable transitional portion which induces internal tension may influence the conductance of the at least one conductive track. Hence, an actuation of the deflectable measurement section may be reliably detected. Preferably, the conductive track is at least partially arranged in a transitional portion where the deflectable measurement section is coupled with the surrounding substrate board. Hence, the transition region which is exposed to considerable strain may be used for the displacement detection. In other words, the displacement of the displacement-sensitive structure is mediately detected by measuring the strain at the transitional portion.

In yet another exemplary embodiment of the transducer, the displacement-sensitive structure comprises at least one conductive polymer thick-film trace that is associated with the deflectable measurement section. Hence, the conductive track may be formed by at least one thick-film trace from conductive polymer material. Thick-film traces may be for instance formed at the substrate board by printing. Other manufacturing techniques for providing the thick-film traces may be envisaged.

In yet another exemplary embodiment of the transducer, the displacement measurement arrangement comprises double-sided displacement-sensitive structures arranged on opposite sides of the substrate board. This may even further increase the measurement accuracy and reliability. For instance, at a first side, the displacement-sensitive structure may be stretched when the deflectable measurement section is actuated. On the opposite side of the substrate board, the displacement-sensitive structure may be squeezed.

In yet another exemplary embodiment of the transducer, the displacement measurement arrangement comprises a plurality of measurement sections disposed over the substrate board. This may have the advantage that multi axis measurement may be achieved which further increases measurement accuracy and reliability.

In still another exemplary embodiment of the transducer, the displacement measurement arrangement is coupled with a compensation control unit that is arranged to compensate a uterine activity signal, wherein signal compensation involves at least one of drift compensation and offset compensation.

Preferably, the compensation control unit may be at least partially provided as an circuitry component of the substrate board. Hence, also the compensation control unit may be integrally provided and/or incorporated at the transducer. The compensation control unit enables a software-based signal compensation. This aspect is based on the insight that the displacement measurement arrangement, particularly the displacement-sensitive structure and the deflectable measurement section, is susceptible to drift, particularly temperature drift, humidity drift, or pressure drift if the transducer is used under water (when the transducer is used in a bath tube, for instance).

Further, as the transducer may be basically freely arranged at the abdominal portion and secured by a strap or belt, also a wide range of (mechanical) preloading may be present. Preloading may involve a certain range of signal offsets, depending on a current position and state of the transducer at the maternal patient.

For instance, the substrate board, particularly the PCB, may incorporate appropriate sensors, involving temperature sensors, humidity sensors, etc. In this way, the actual performance and characteristics of the displacement measurement arrangement may be monitored. Signals generated and supplied by the sensors may be used to control the compensation measures.

Therefore, applying mathematical methods like statistical analysis, low pass filtering, automatic gain control and/or contraction detection may reduce or even eliminate the need for repeated (manual) check and adjustment. As a result, due to computational control and signal shaping methods, basically considerably inaccurate sensor techniques may be used which are easy to manufacture and also considerably cost-efficient. However, the compensation control unit ensures that the required accuracy and reliability level may be achieved. Further, automatic signal compensation further simplifies operating the transducer as the level of manual intervention may be further decreased.

As a consequence, the displacement measurement arrangement may utilize polymer thick-film resistors, accelerometers, magnetic (inductive) field detectors, capacitive field detectors and further components, depending on an actually implemented displacement measurement principle. Hence, the freedom of design is greatly increased.

In yet another aspect of the present disclosure, a method of operating a maternal monitoring transducer is presented, the method comprising the following steps:
providing a displacement measurement arrangement comprising a displacement-sensitive structure that is arranged to detect deformations of a deflectable measurement section, wherein the deflectable measurement section is integrally formed in a substrate board, particularly a PCB, disposed in a housing of the transducer,
sensing deformations of the displacement-sensitive structure,
supplying a uterine activity signal that is indicative of uterine activity, based on the deformations of the displacement-sensitive structure, and
coupling the displacement measurement arrangement with a compensation control unit that is arranged to compensate the uterine activity signal, wherein signal compensation involves at least one of drift compensation and offset compensation.

Preferred embodiments of the invention are defined in the dependent claims. It shall be understood that the claim method has similar and/or identical preferred embodiments as the claimed device and as defined in the dependent claims.

BRIEF DESCRIPTION OF THE DRAWINGS

These and other aspects of the disclosure will be apparent from and elucidated with reference to the embodiments described hereinafter. In the following drawings

DETAILED DESCRIPTION OF THE INVENTION

In the following, several embodiments of devices and methods that can make use of at least some aspects of the present disclosure will be presented and elucidated in more detail.

Figure 1:
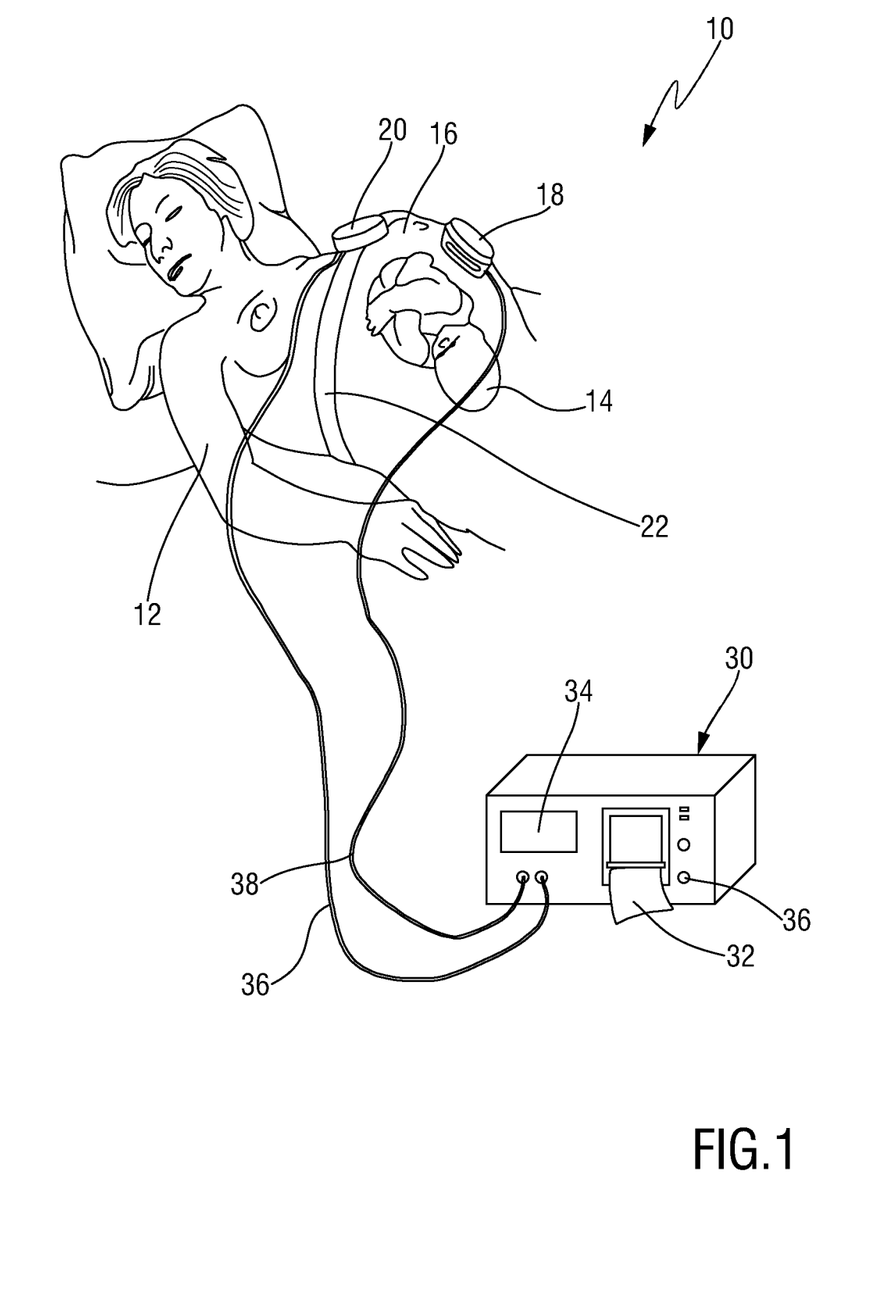
FIG. 1 shows a simplified schematic illustration of a monitoring system according to an embodiment of the present disclosure.

FIG. 1 is a schematic simplified view of a monitoring system 10 that is used to monitor the well-being of a pregnant patient and the fetus. The system 10 may be also referred to as fetal monitoring system or as maternal and fetal monitoring system.

More particularly, at least in some embodiments, the system 10 may be referred to as CTG monitoring system.

The system 10 comprises transducers that are attached to the patient 12 so as to monitor health indicative signals. The system 10, at least in some embodiments, monitors physiological signals of the maternal patient 12 and the fetus 14 in the abdominal portion 16.

By way of example, the system 10 comprises a fetal monitoring transducer 18 and a maternal monitoring transducer 20. In accordance with the exemplary embodiment illustrated in FIG. 1, the fetal monitoring transducer 18 is arranged to monitor the heart rate of the fetus 14. To this end, the transducer 18 may be arranged as an ultrasonic transducer. For instance, the maternal monitoring transducer 20 may be arranged to monitor uterine activity, particularly uterine contractions, of the maternal patient 12. To this end, the transducer 20 may involve a strain-sensitive and/or displacement sensitive sensor, as will be discussed in more detail herein further below.

The transducers 18, 20 may be placed at the abdomen 16 of the patient 12. For instance, the transducer 20 as shown in FIG. 1 is secured by a belt or strap 22. Depending on the actual posture and condition of the patient 12 and the fetus 14, a proper position and placement for the transducers 18, 20 may be chosen. Also the transducer 18 may be secured by a strap.

The system 10 further comprises a control unit 30 which is arranged to receive signals monitored by the transducers 18, 20. The control unit 30 is arranged to provide a plot 32, particularly a so-called CTG plot. Further, the control unit 30 may be provided with a display 34, user controls 36 for operating the system 10, etc.

Via signal cables 36, 38, the transducers 18, 20 are coupled with the control unit 30. Hence, in accordance with the exemplary embodiment illustrated in FIG. 1, the transducers 18, 20 are arranged as wired transducers. However, in alternative embodiments, so-called wireless transducers may be envisaged that communicate with the control unit 30 in a wireless fashion.

Figure 2:
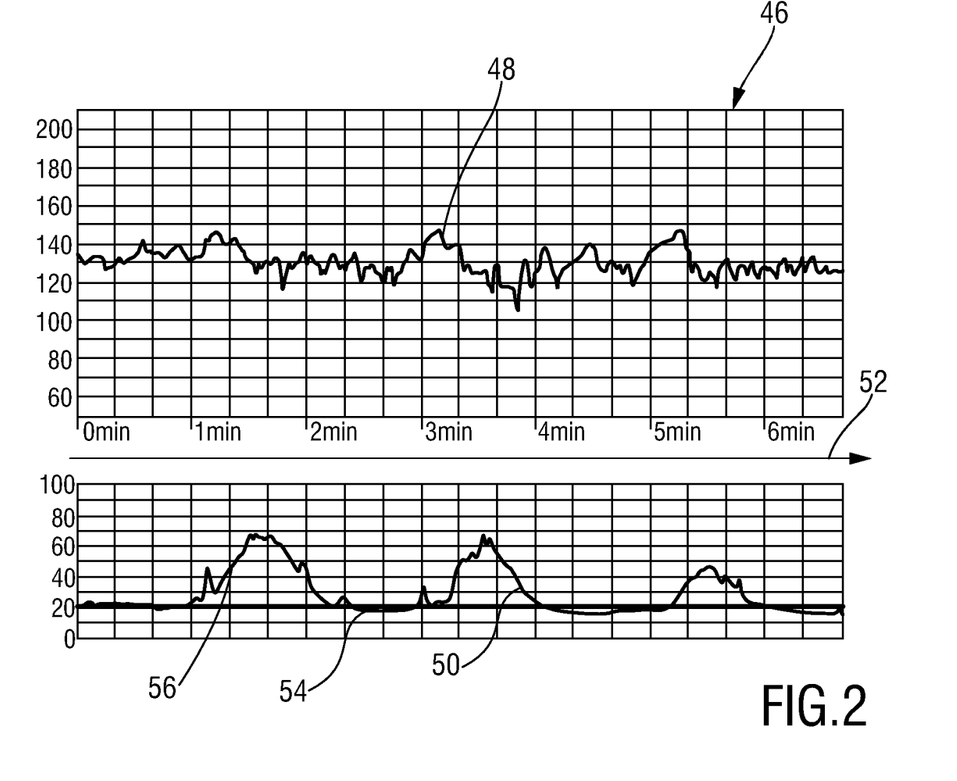
FIG. 2 shows a simplified illustration of an exemplary CTG plot involving fetal information and maternal information.

In FIG. 2, an exemplary CTG plot 46 is illustrated. The plot 46 involves two sections including a signal trace 48 that displays a fetal heart rate-indicative signal. Further, a signal trace 50 may be provided which displays a uterine activity-indicative signal. A time axis is indicated by reference numeral 52.

In accordance with the present disclosure, the detection of uterine activity is of particular interest. Overall, monitoring both the fetal heart rate and the uterine activity may allow conclusions to be drawn as to the general state of health and stress level of the fetus 14. Further, a correlation of uterine contractions (labor) and a responding increase or decrease in the heart rate of the fetus 14 may be monitored.

The uterine activity-indicative signal trace 50 includes a baseline 54 indicating periods of little or no uterine activity and periods 56 of uterine activity including characteristic peaks. For instance, a peak interval of the uterine activity signal 50 is indicative of the progress of delivery.

Figure 3:
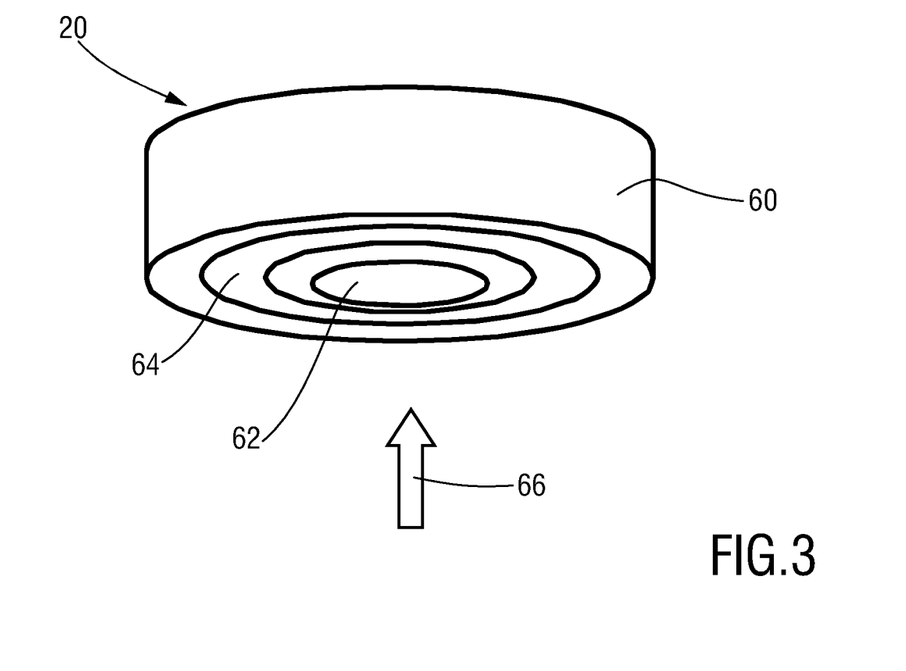
FIG. 3 is a simplified schematic perspective bottom view of a maternal monitoring transducer in accordance with an embodiment of the present disclosure.

Further reference is made to FIG. 3 illustrating a simplified schematic perspective bottom view of a maternal monitoring transducer 20 that is arranged to monitor uterine activity, particularly uterine contractions. The transducer 20 includes a housing 60. Further, the transducer 20 incorporates a sensing section 62. The sensing section is actuable (displaceable) when the respective side of the housing 60 is attached to the abdomen 16 of the female patient 12. In other words, the sensing section 62 may be deflected and/or displaced in response to muscular uterine activity. By way of example, the housing 60 is arranged in a discoid or cylindrical fashion, wherein the sensing section 62 is arranged at a frontal side thereof facing the abdomen 16. So as to allow for the deformability and/or movability of the sensing section 62, a diaphragm 64 may be provided. Hence, the sensing section 62 may be actuated and displaced relative to the remaining portion of the housing 60.

By way of example, the sensing section 62 may be arranged as sensing head or sensing knob. The sensing section 62 may be arranged as push button.

In FIG. 3, a block arrow 66 indicates a direction of an actuating force when a uterine contraction is present. However, as the transducer 20 is typically attached to the abdomen 16 using a belt or strap 22, also a certain level of preloading may be present that is applied to the sensing section 62. This may further involve a respective drift or changes of the preloading when the transducer 20 slips out of place or is deliberately displaced along the abdomen 16. Caregivers and midwives regularly seek for better signals by shifting the position of the transducer 20 when the respective signal trace 50 (FIG. 2) is not yet sufficiently conclusive.

Figure 4:
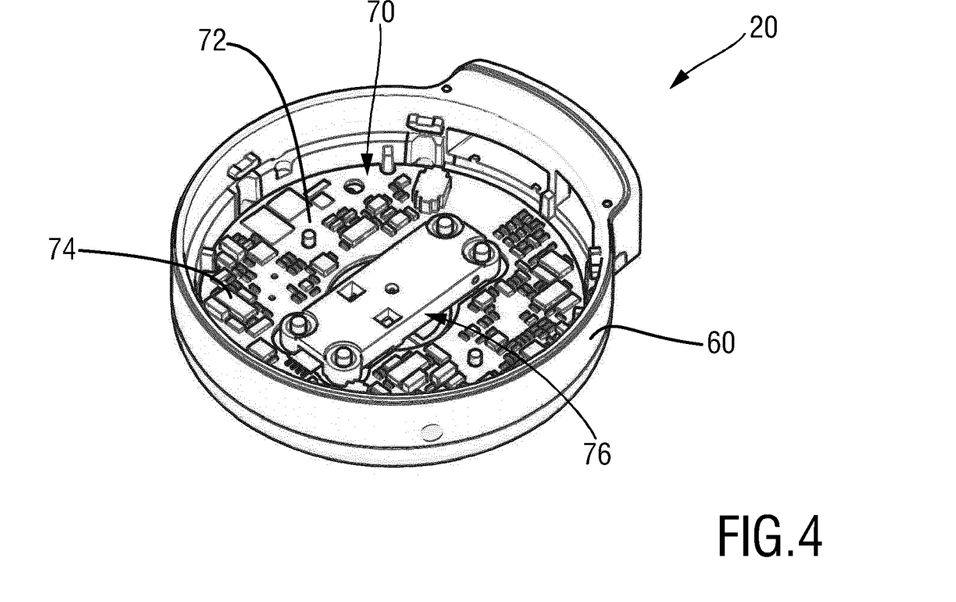
FIG. 4 is a simplified perspective view of a maternal monitoring transducer according to an embodiment of the present disclosure, wherein a cover is omitted for illustrative purposes.

FIG. 4 illustrates an interior of an exemplary embodiment of a fetal monitoring transducer 20. In FIG. 4 a perspective top view of the transducer 20 is provided. A housing bottom wall of the transducer 20 is omitted for illustrative purposes.

In the housing 60 of the transducer 20, a printed circuit board (PCB) 70 is provided that involves a substrate board 72. By way of example, the substrate board 72 may be made from composite material involving fiberglass cloth that is impregnated with an epoxy resin. For instance, so-called FR4 material may be used. Several circuitry components 74 are attached to or formed in the substrate board 72. Hence, the transducer 20 as such may already provide a certain computing and control capability. An important component of the transducer 20 is the uterine activity sensor as such. For instance, a so-called displacement measurement arrangement 76 may be provided which is at least partially integrated in the substrate board 72 of the PCB 70. In other words, at least a major component of the displacement measurement arrangement 76 may be integrally formed with or provided by the substrate board 72. This involves that at least a portion of the substrate board 72 is arranged in a displaceable and/or deflectable fashion so as to detect uterine contractions which may be converted into a respective signal (signal trace 50 in FIG. 2).

In accordance with the present disclosure, the displacement measurement arrangement 76 is not arranged as a separate sensor that is merely attached to the substrate board 72. Rather, the substrate board 72 is, at least in part, an inherent component of the displacement measurement arrangement 76.

Figure 5:
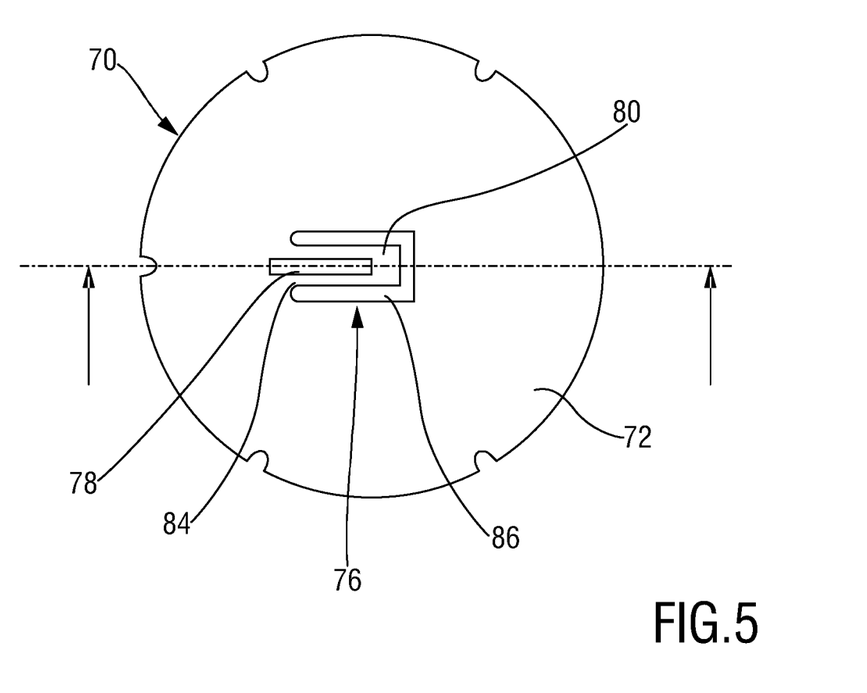
FIG. 5 is a simplified schematic top view of a substrate board according to an embodiment of a maternal monitoring transducer of the present disclosure.

FIG. 5 shows a simplified top view of a substrate board 72 that forms a PCB 70. At the substrate board 72, the displacement measurement arrangement 76 is provided. The arrangement 76 involves a displacement sensitive structure 78 that is arranged to detect deformations and/or deflections of a deflectable measurement section 80. The deflectable measurement section 80 may be arranged as a lug or tab formed in the substrate board 72. As shown in FIG. 5, the deflectable measurement section 80 is encompassed or surrounded by a recess 86.

At a transitional portion 84, the deflectable measurement section 80 is connected with a surrounding region of the substrate board 72. Needless to say, the deflectable measurement section 80 does not necessarily have to be arranged in a central region of the substrate board 72. Rather, the deflectable measurement section 80, at least in some exemplary embodiments, may be arranged at a boundary region of the substrate board 72.

The material from which the substrate board 72 is formed is generally resilient and arranged in an elastic fashion. Hence, in response to an application of force to the deflectable measurement section 80, a certain deformation of the deflectable measurement section 80 is present, whereas the deflectable measurement section 80 returns to an original position when no force is applied thereto. Also the displacement sensitive structure 78 is exposed to the deformations/deflections. Hence, by appropriate circuitry and sensory arrangements, a signal may be generated that is indicative of a current degree of deflection/deformation and, consequently, of a current level of uterine activity.

In contrast to prior art transducers, no separate, additional strain/deflection measurement element is used. Rather, an inherent section of the substrate board 72 is mechanically actuable or manipulable and therefore forms a major component of the displacement measurement arrangement 76.

Several principles may be used to detect deformations/deflections of the deflectable measurement section 80. This may involve, for instance, capacitive sensing, inductive sensing, conductivity sensing, accelerometer sensing, Eddy-current sensing, etc.

Figure 6:
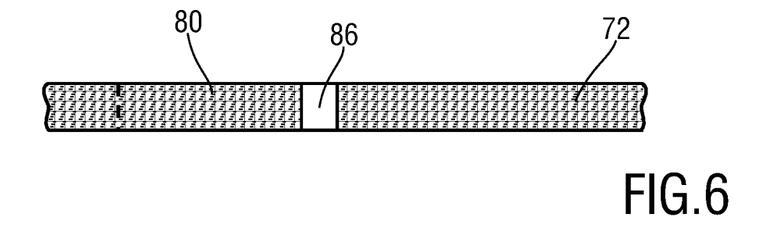
FIG. 6 is a simplified schematic cross-sectional partial side view of a substrate board in a first non-deflected state.
Figure 7:
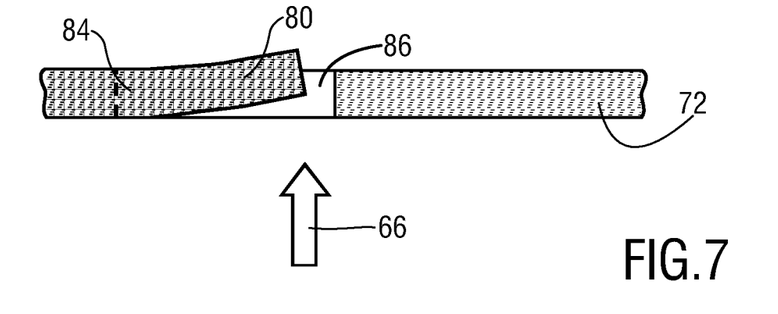
FIG. 7 is further simplified schematic cross-sectional partial side view of the substrate board of FIG. 6 in a second, deflected state.

With reference to FIGS. 6 to 9, several measurement principles will be illustrated. FIGS. 6 to 9 illustrate a partial cross-sectional view through an exemplary embodiment of a displacement measurement arrangement 76. An orientation of the views of FIGS. 6 to 9 is indicated in FIG. 5 by a dot-dashed line. In FIGS. 6 and 7, primarily the substrate board 72 is illustrated, wherein a deflectable measurement section 80 is shown in FIG. 6 in a non-deflected state and in FIG. 7 in a deflected state, in response to an application of force (reference numeral 66).

Figure 8:
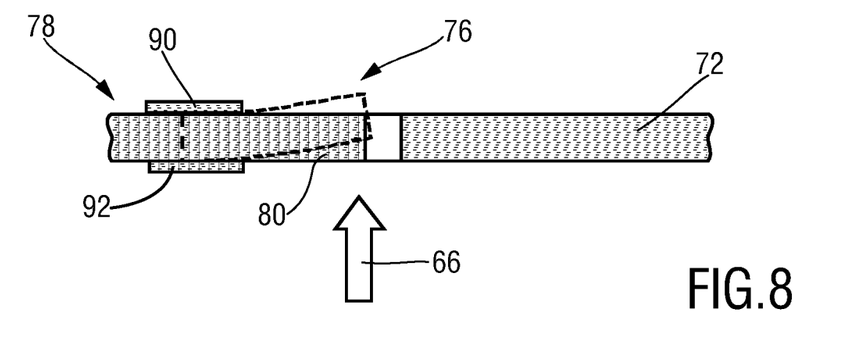
FIG. 8 illustrates in a partial cross-sectional side view a first embodiment of a displacement measurement arrangement arranged at a substrate board.
Figure 9:
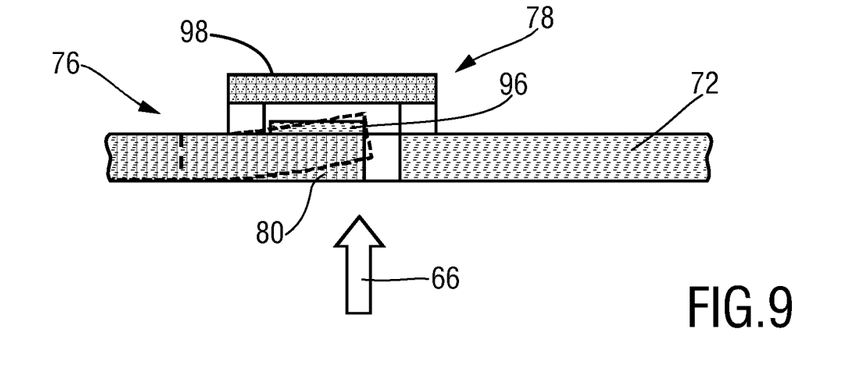
FIG. 9 illustrates in a partial cross-sectional side view a second embodiment of a displacement measurement arrangement arranged at a substrate board.

In FIG. 6 and FIG. 7, the displacement sensitive structure 78 is not explicitly shown. FIG. 8 and FIG. 9 illustrate exemplary embodiments of the displacement measurement arrangement 76. In FIG. 8 and FIG. 9, the deflected state of the deflectable measurement section 80 is indicated by dashed lines.

In FIG. 8, the displacement sensitive structure 78 involves conducting tracks 90, 92 which are associated with the transitional portion 84 that connects the deflectable measurement section 80 and a main portion of the substrate board 72. Consequently, the deflection of the deflectable measurement section 80 which causes a deformation of the transitional portion 84 is sensed in a mediate fashion. When the deflectable measurement section 80 is deflected, one of the conducting tracks 90, 92 is squeezed, while the other one is stretched. The deformation of the conducting tracks 90, 92 may have an influence on the conductance thereof, and may be sensed by appropriate circuitry. As indicated further above, the conductive tracks 90, 92 may be arranged as conductive polymer tracks. More particularly, the tracks 90, 92 may be arranged as conductive polymer thick-film traces.

FIG. 9 illustrates an alternative embodiment of the displacement measurement arrangement 76, wherein the displacement sensitive structure 78 involves an inductive coil 96 that is arranged to be displaced/moved with respect to a reference element 98. Hence, an inductive proximity sensor is provided that is at least partially integrally shaped with the substrate board 72. Similarly, also a capacitive proximity/motion sensor may be provided, wherein reference numerals 96, 98 would in this case represent respective electrodes.

As indicated above, also accelerometer sensors, Eddy-current sensors and further appropriate types of displacement/deformation sensors may used and attached, at least in part, to the deflectable measurement section 80.

Further, in some exemplary embodiments, several types of sensors for sensing the deflection and/or strain of the deflectable measurement section 80 are combined. This may enable an even more precise and reliable detection of maternal motion.

Figure 10:
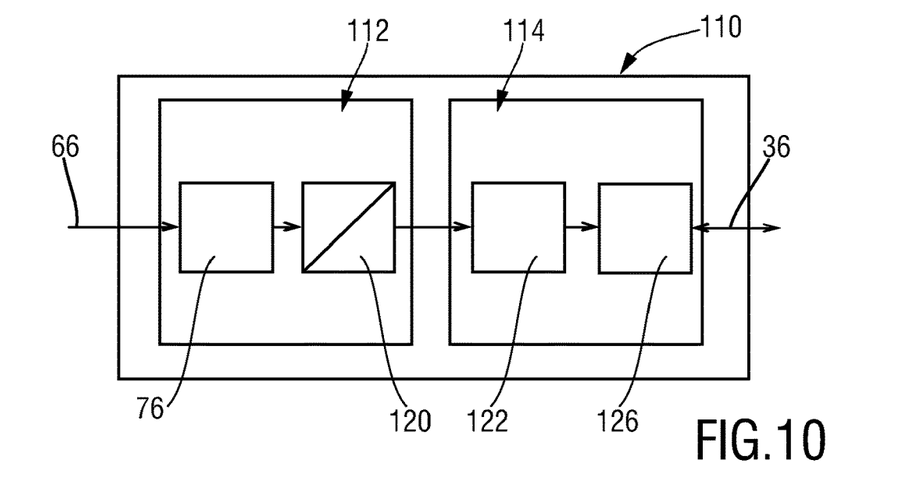
FIG. 10 is a schematic block diagram illustrating an exemplary embodiment of a control unit for a maternal monitoring transducer.

FIG. 10 illustrates by means of a block diagram a schematic simplified layout of a control unit 110 for the transducer 20. The control unit 110 may be at least partially provided and formed at the substrate board 72. The control unit 110 involves an analog control section 112 and a digital control section 114. In some embodiments, the digital control section 114 may be referred to as compensation control unit.

The analog section 112 is arranged to detect the (input) force that causes a deflection of the deflectable measurement section 80 of the displacement measurement arrangement 76. The displacement measurement arrangement 76 involves a respective sensor which may be arranged as an inductive sensor, a capacity sensor and/or a conductance/conductivity sensor.

The displacement measurement arrangement 76 is arranged to provide an analog (electric) signal which is fed to an A/D converter 120. Hence, a digital signal that represents an actual state of deflection/deformation end, consequently, an actual level of uterine activity is provided.

In the digital control section 114, a signal processor 122 is provided. The signal processor 122 may involve a single processor or a distributed arrangement involving a plurality of processors. The signal processor 122 is arranged to process and shape the digital signal provided by the A/D converter 120. Exemplary signal processing measures will be discussed further below. Downstream of the signal processor 122, an interface 126 is provided which may be coupled with the (overall) control unit 30 of the monitoring system 10 by a cable 36, refer also to FIG. 1, or in a wireless fashion.

It has been detected that properties and characteristics of the substrate board 72 and of further components of the displacement measurement arrangement 76 involving the displacement sensitive structure 78 are somewhat unsteady and subject to variations in response to temperature changes, humidity changes, etc. Therefore, it may not be unlikely that the detected signal (refer to the signal trace 50 in FIG. 3) is somewhat corrupted and/or distorted, involving offset and drift phenomena. This applies in particular when environmental conditions are unsteady.

Further, as discussed above, the transducer 20 as such is typically not fixedly attached to the abdomen 16 of the subject 12. Rather, a somewhat flexible unsteady attachment is used, taking account of the current posture and state of the maternal patient 12 and the fetus 14. Also the subject 12 is typically not resting in a perfectly immobile fashion.

It is also noted that CTG monitoring typically takes a certain time period, for instance half an hour or even longer. Therefore, it may not be totally unlikely that a certain drift of further distortions are present in the detected uterine activity-indicative signal.

Figure 11:
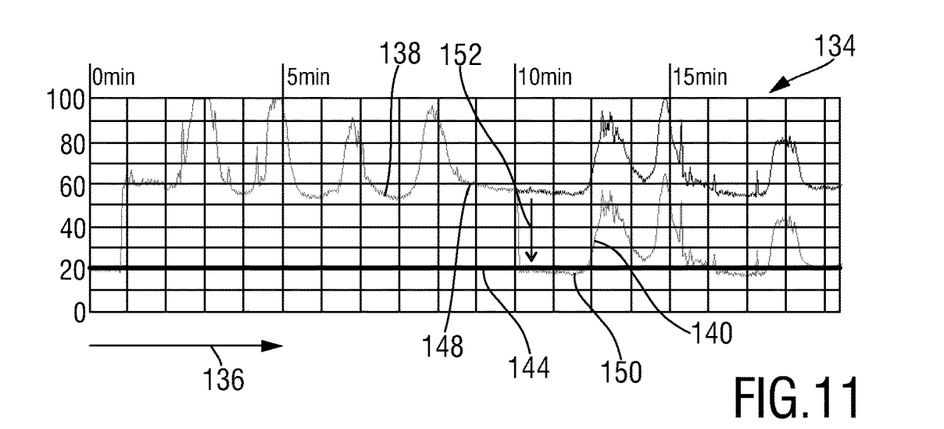
FIG. 11 shows a simplified illustration of an exemplary CTG plot involving maternal information represented by a first, distortion-afflicted plot and a second, compensated plot.
Figure 12:
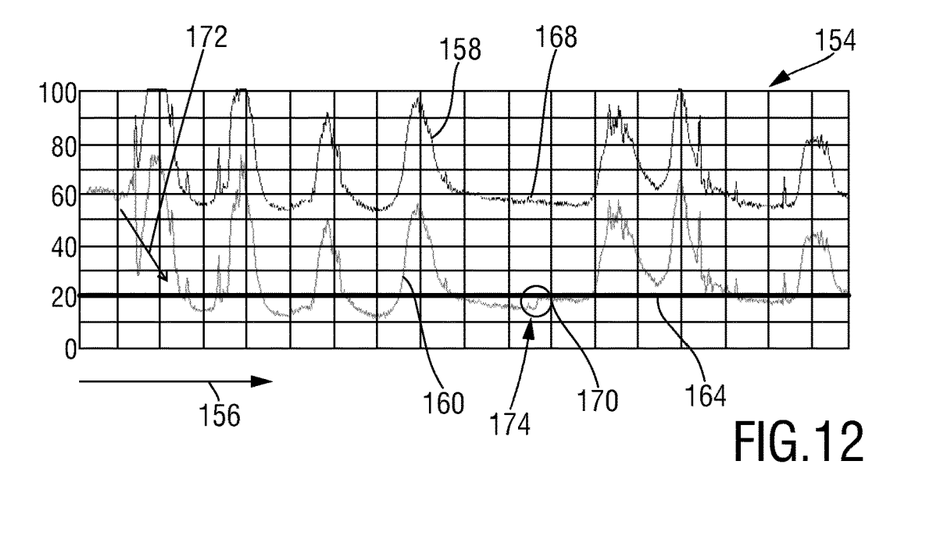
FIG. 12 shows a simplified illustration of a further exemplary CTG plot involving maternal information represented by a first, distortion-afflicted plot and a second, compensated plot.

Therefore, it is proposed to apply compensation algorithms to the signal provided by the A/D converter 120. With reference to FIG. 11 and FIG. 12, exemplary signal compensation/shaping measures will be presented. FIG. 11 shows a signal trace 134. FIG. 12 shows a signal trace 154. Both signal traces 134, 154 may be referred to as uterine activity/contractions traces and may therefore form a part of a CTG plot.

In FIG. 11, a time axis is indicated by 136. In FIG. 12, a time axis is indicated by 156. In FIG. 11, a distortion containing (original) signal is indicated by 138. In FIG. 12, a distortion containing (original) signal is indicated by 158. In FIG. 11 and FIG. 12, an assumed (calculated) baseline range is indicated by 144 and 164, respectively. The baseline ranges 144, 164 shall represent a state where no uterine contractions are present. It is recalled in this context that the uterine activity traces 134, 154 typically involve a relative or arbitrary scale as generally an unpredictable level of preloading is present at the transducer 20. Therefore, signal processing measures may be applied that align an actual baseline 148, 168 of the signals 138, 158 with the baseline range 144, 164.

In FIG. 11, the (original) distorted signal 138 is subject to an offset distortion (left portion of chart). Reference numeral 152 indicates a compensating event, wherein the signal is aligned with the baseline range 144. In FIG. 12, a similar compensation is performed at the compensating event 172. In FIG. 11, a respectively compensated signal is indicated by 150. In FIG. 12, a respectively compensated signal is indicated by 160. As a result of the baseline/offset compensation, the compensated baseline 150, 170 is aligned with the preferred baseline range 144, 164. Offset compensation may involve shifting and scaling the signals.

In some exemplary embodiments, compensation events are marked in the CTG plot (reference numeral 46 in FIG. 2), for instance with a marker character on the record to indicate corrections caused by the signal processing. Hence, further augmented information may be provided in the CTG plot and used for interpreting the measured data.

In FIG. 12, a further corrective event is indicated by 174. The compensating event 174 involves drift compensation. As can be seen in FIG. 12, a slight drift is present in the signals which may be for instance attributable to temperature and/or humidity changes. Hence, the signal baseline 170 is again aligned with the preferred baseline range 164.

Figure 13:
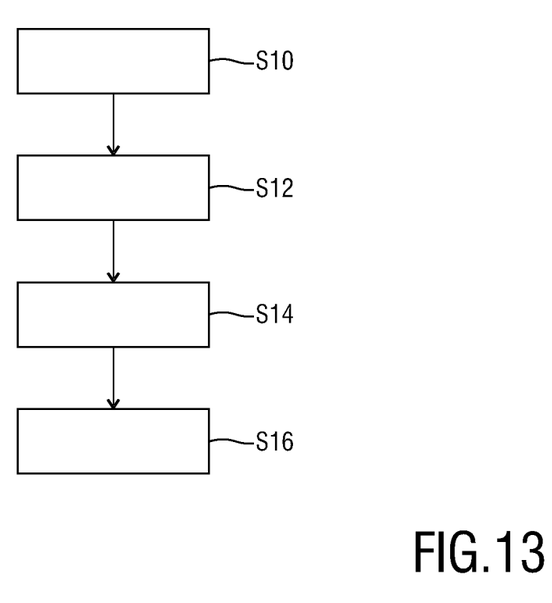
FIG. 13 shows an illustrative block diagram representing several steps of an embodiment of a method in accordance with the present disclosure.

Further reference is made to FIG. 13 showing a block diagram illustrating several steps of an exemplary embodiment of a method in accordance with the present disclosure.

The method contains a step S10 involving a provision of a displacement measurement arrangement at a maternal monitoring transducer. Preferably, the displacement measurement arrangement involves a displacement-sensitive structure that is arranged to detect deformations of a deflectable measurement section, wherein the deflectable measurement section is integrally formed/provided in a substrate board of the transducer. In other words, a substrate board, particularly a PCB which is anyway provided at the transducer, may be advantageously used for deflection/deformation measurement.

In a further step S12, deformations and/or deflections of the displacement-sensitive structure are sensed, wherein the deformation/deflections are attributable to respective actuations of the deflectable measurement section.

In a further step S14, a corresponding original signal, particularly a uterine activity signal is supplied which is indicative of uterine activity. The signal is based on the deformations/deflections of the deflectable measurement section sensed by the displacement-sensitive structure.

In yet another step S16, the displacement measurement arrangement is coupled with a compensation control unit which is preferably provided at the substrate board as well. The compensation control unit is arranged to compensate the original signal. Preferably, signal compensation involves at least one of drift compensation and offset compensation.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A maternal monitoring transducer comprising:
a housing;
a substrate board with circuitry components disposed in the housing, wherein the substrate board comprises a recess that defines a deflectable measurement section, which is integrally formed in the substrate board, such that the deflectable measurement section is connected with a surrounding region of the substrate board at a transitional portion and is separated from the surrounding region by the recess opposite the transitional portion, enabling deformations of the deflectable measurement section relative to the surrounding region in response to actuating forces on the deflectable measurement section; and
a displacement measurement arrangement at least partially integrated into the substrate board, wherein the displacement measurement arrangement comprises a displacement-sensitive structure that is arranged to detect the deformations of the deflectable measurement section of the substrate board,
wherein the displacement measurement arrangement is arranged to supply a uterine activity signal indicative of uterine activity based on the detected deformations.

2. The transducer as claimed in claim 1, wherein the maternal monitoring transducer is a pressure sensitive transducer.

3. The transducer as claimed in claim 1, wherein the displacement-sensitive structure of the displacement measurement arrangement is directly attached to the substrate board.

4. The transducer as claimed in claim 1, wherein the displacement-sensitive structure of the displacement measurement arrangement is embedded in the substrate board.

5. The transducer as claimed in claim 1, wherein the recess forms a gap in the substrate board around three sides of the deflectable measurement section.

6. The transducer as claimed in claim 1, wherein the housing further comprises a contact section that contacts an abdominal portion when the transducer is applied to a maternal patient; and wherein the deflectable measurement section is operatively coupled with the contact section.

7. The transducer as claimed in claim 1, wherein the displacement-sensitive structure comprises an inductive coil and a reference element, and wherein the deformations of the deflectable measurement section involve relative motion between the inductive coil and the reference element.

8. The transducer as claimed in claim 1, wherein the displacement-sensitive structure comprises a movable electrode and a reference electrode, and wherein the deformations of the deflectable measurement section involve relative motion between the movable electrode and the reference electrode.

9. The transducer as claimed in claim 1, wherein the displacement-sensitive structure comprises at least one conductive track associated with the deflectable measurement section.

10. The transducer as claimed in claim 1, wherein the displacement-sensitive structure comprises at least one conductive polymer thick-film trace associated with the deflectable measurement section.

11. The transducer as claimed in claim 1, wherein the displacement-sensitive structure comprises double sided displacement-sensitive structures arranged on opposite sides of the substrate board.

12. The transducer as claimed in claim 1, wherein the displacement measurement arrangement comprises a plurality of measurement sections disposed over the substrate board.

13. The transducer as claimed in claim 1, wherein the displacement measurement arrangement is coupled with a compensation controller that is arranged to compensate the uterine activity signal, wherein the signal compensation involves at least one of drift compensation or offset compensation.

14. The transducer as claimed in claim 1, wherein the deflectable measurement section comprises a lug or a tab formed in the substrate board.

15. The transducer as claimed in claim 1, wherein the displacement-sensitive structure is arranged to detect deformations of the deflectable measurement section of the substrate board using capacitive sensing, inductive sensing, conductivity sensing, accelerometer sensing, or Eddy-current sensing.

16. A method of operating a maternal monitoring transducer, the method comprising:
    providing a substrate board with circuitry components, wherein the substrate board comprises a recess that defines a deflectable measurement section, which is integrally formed in the substrate board, such that the deflectable measurement section is connected with a surrounding region of the substrate board at a transitional portion and is separated from the surrounding region by the recess opposite the transitional portion, enabling deformations of the deflectable measurement section relative to the surrounding region in response to actuating forces on the deflectable measurement section;
    providing a displacement measurement arrangement at least partially integrated into the substrate board, the displacement measurement arrangement comprising a displacement-sensitive structure;
    detecting the deformations of the deflectable measurement section using the displacement-sensitive structure; and
    supplying a uterine activity signal indicative of uterine activity, based on the detected deformations of the deflectable measurement section.

17. The method as claimed in claim 16, further comprising:
    compensating the uterine activity signal using a compensation controller coupled to the displacement measurement arrangement, wherein compensating the uterine activity signal involves at least one of drift compensation or offset compensation.

18. The method as claimed in claim 16, wherein the displacement-sensitive structure comprises an inductive coil and a reference element, and wherein detecting the deformations of the deflectable measurement section comprises detecting relative motion between the inductive coil and the reference element.

19. The method as claimed in claim 16, wherein the displacement-sensitive structure comprises a movable electrode and a reference electrode, and wherein detecting the deformations of the deflectable measurement section comprises detecting relative motion between the movable electrode and the reference electrode.

20. The method as claimed in claim 16, wherein the displacement-sensitive structure comprises conductive tracks associated with the deflectable measurement section, and wherein detecting the deformations of the deflectable measurement section is based on squeezing and stretching of the conductive tracks.

* * * * *